United States Patent [19]

Uzgiris et al.

[11] 4,217,195
[45] Aug. 12, 1980

[54] ELECTROPHORETIC ELECTRODE FOR USE IN LASER DOPPLER SHIFT SPECTROSCOPY, AND METHOD

[75] Inventors: Egidijus E. Uzgiris; John A. Bergeron, both of Schenectady, N.Y.

[73] Assignee: General Electric Company, Schenectady, N.Y.

[21] Appl. No.: 35,229

[22] Filed: May 2, 1979

[51] Int. Cl.² ............................................. G01N 27/30
[52] U.S. Cl. ............................ 204/195 F; 204/180 R; 204/299 R; 204/290 F
[58] Field of Search .................. 204/195 F, 47, 195 P, 204/290 F, 180 R, 299 R

[56] References Cited

U.S. PATENT DOCUMENTS

| 2,183,531 | 12/1939 | Allison | 204/195 F |
|---|---|---|---|
| 3,234,110 | 2/1966 | Beer | 204/47 X |
| 3,461,044 | 8/1969 | Lyons, Jr. et al. | 204/47 X |
| 3,591,482 | 7/1971 | Neff et al. | 204/195 F |
| 3,766,048 | 10/1973 | Flygare et al. | 204/299 R |
| 3,783,117 | 1/1974 | Bean | 204/180 R |
| 3,905,889 | 9/1975 | Macur et al. | 204/195 P X |
| 3,984,533 | 10/1976 | Uzgiris | 204/299 R X |
| 4,011,044 | 3/1977 | Uzgiris | 204/299 R X |
| 4,070,504 | 1/1978 | Bianchi et al. | 204/290 F X |
| 4,101,220 | 7/1978 | Bean et al. | 204/299 R X |
| 4,113,596 | 9/1978 | Treille et al. | 204/180 R |

OTHER PUBLICATIONS

Uzgiris, "Laser Doppler Spectrometer for Study of Electrokinetic Phenomena", Rev. Sci. Instrum., vol. 45, No. 1, Jan. 1974, pp. 74–80.

*Primary Examiner*—Arthur C. Prescott
*Attorney, Agent, or Firm*—Leo I. MaLossi; James C. Davis, Jr.

[57] ABSTRACT

By means of a thin, porous polymer overcoating, the surface of a silver-silver chloride reversible electrode is adequately stabilized for use at high current densities in electrophoretic analysis applications.

11 Claims, 6 Drawing Figures

ELECTROPHORETIC ELECTRODE FOR USE IN LASER DOPPLER SHIFT SPECTROSCOPY, AND METHOD

The present invention relates generally to electrophoretic analysis of biological materials and is more particularly concerned with novel electrodes having special utility in laser Doppler shift spectroscopy and is also concerned with new methods of producing such electrodes.

BACKGROUND OF THE INVENTION

Electrophoretic analysis requires the application of an electric field to a suspension of macromolecules or cells being studied. In the highly sensitive method disclosed and claimed in U.S. Pat. No. 3,984,533, assigned to the assignee hereof, which involves the Doppler shift of scattered coherent light, endosmotic flow and Joule-heating convective flow are limited by closely spacing the electrodes. When in ideal circumstances the electrode gap is only about one millimeter in width, electrode pH stability and surface stability against release of particles are of major importance particularly in terms of resolution of the laser Doppler shift spectrometer. Electrodes of conventional design and construction do not satisfy these requirements, the electrically reversible silver-silver chloride type release colloidal particles into the probed volume which interfere with light scattering measurements. Non-reversible platinum-platinum black electrodes, on the other hand, do not present the surface instability problem but lack pH stability even under symmetrical application of a square wave electrical field. This pH drift effect can be reduced but by no means eliminated through the application of a coating of protein such as bovine serum albumin and the necessity for constant monitoring of electrode performance remains.

SUMMARY OF THE INVENTION

In accordance with this invention based upon our new concepts and discoveries set out below, novel electrophoretic analysis electrodes are provided which are free from the short-comings of those of the prior art described above. Moreover, this invention involves no substantially offsetting disadvantage, the desirable features of the prior invention being retained and in some instances actually enhanced substantially.

One of our new concepts is the application of a thin coat or film of a low charge polymer gel over the surface of a silver-silver chloride electrode. Thus, we have found that a sponge-like agarose gel film is effective to prevent emission of silver chloride particles into the testing solution even at relatively high current densities and over protracted periods of operation.

Another of our new concepts is the combination of a silver-silver chloride electrode with a platinum black electrode in a new hybrid structure in which the platinum black is bonded directly to the metallic surface of the silver electrode. A coating of porous gel film as described above is applied to the resulting platinum black coated body. Again, we have found that the film allows formation in situ of silver chloride on the silver surface exposed through the discontinuous platinum black coating but also serves as previously described to prevent emission of silver chloride particles into the test solution during normal use of the electrode in electrophoretic analysis operations.

Still another concept of ours is to control the polymer film thickness and to ensure its thickness uniformity through the use of a solution of the polymer film source and by regulation of the concentration of that source in the solution. In this connection, we have found that a two percent agarose composition in molten form at a temperature of about 80° C. serves particularly well for the purposes of this invention.

Finally, we have found that an electrode prepared in accordance with this invention with a coating of organic polymer or similar gel can be platinized after applying the gel coating without impairment of the basic function of the electrode but with improvement in its overall service performance.

Described in brief, then, an electrode of this invention comprises a body of suitable material such as silver having either a suitable metal compound coating such as silver chloride or platinum black and a gel overcoating or having a gel coating and a platinum black overcoating, the gel coating in either case being of resistivity of less than about $2 \times 10^{-2}$ ohm centimeter measured in physiological saline solution and being of substantially uniform thickness overall approximating 10 to 100 micrometers, preferably about 25 micrometers.

Similarly, briefly stated, the method of this invention includes the step of providing the chosen metallic electrode body with a thin coating or film of gel-forming material and thereafter converting the latter into a gel. This coating is applied either directly to the electrode body surface or is overcoated on the metallic compound of the electrode metal-metal compound combination.

DETAILED DESCRIPTION OF THE INVENTION

Figure 1:
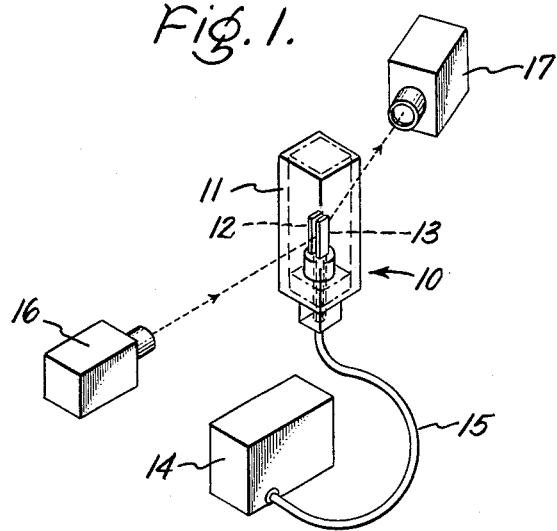
FIG. 1 is a schematic view of an optical Doppler electrophoretic measurement system incorporating the novel electrodes of this invention.

Measurement of electrophoretic mobilities by detecting laser or coherent light scattering by particles in the probed volume is accomplished through the use of system illustrated in FIG. 1, the central component of which is electrophoretic cell 10 in which the test solution is contained in a glass or light transmissive plastic vessel 11. Closely-spaced electrodes 12 and 13 are disposed within vessel 11 and, as shown, are preferably of rectangular shape, their opposed surfaces defining a gap not exceeding one millimeter in width.

Vessel 11 is filled with a solution containing the biological material particles to be electrophoretically analyzed. By means of power supply 14, an electric field is established between electrodes 12 and 13 electrically connected to the power supply in the usual manner by leads within cable 15. A beam of coherent optical energy is directed into the gap between electrodes 12 and 13 by means of laser generator 16. Part of the optical energy is scattered within the gap and because of the motion of the scattering particles in the electric field, exhibits a Doppler frequency shift. Optical energy scattered at a predetermined angle is received by optical detector 17 which is preferably a photomultiplier tube.

Figure 2:
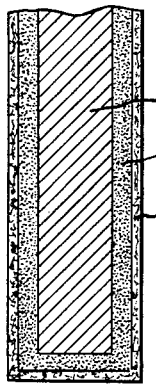
FIG. 2 is an enlarged, fragmentary cross-sectional view of a silver-silver chloride reversible electrode of this invention.

As shown in FIG. 2, the silver-silver chloride electrode is in the form of a silver strip about 0.5 mm thick, the surface of which is covered with an adherent film 21 of silver chloride approximately 25 $\mu$m thick. A gel coating approximately 20 $\mu$m thick of resistivity approximating $1.5 \times 10^{-2}$ ohm centimeter (in physiological saline solution) covers the entire electrode surface as an overcoating on the silver chloride coat. In this illustration, the thickness of gel coating 22 is grossly exaggerated for purposes of illustrating the nature of the gel which is actually sponge-like. As indicated above, this open construction of the gel does not prevent it from effectively performing its main function of preventing emission of silver chloride particles from the electrode into the solution surrounding the electrode during use. As also indicated above, gel film 22 in no way diminishes the sensitivity or other performance characteristics of the electrode system in which the electrode is used.

Figure 3:
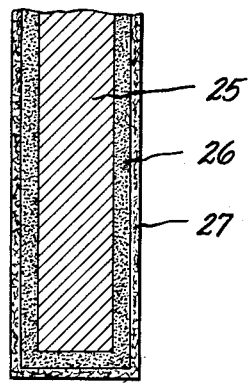
FIG. 3 is an enlarged, fragmentary cross-sectional view of a silver platinum black electrode of this invention.

The electrode of FIG. 3 likewise comprises a thin silver strip 25 but in this case the silver surface is covered by a discontinuous film 26 of platinum black which in turn is overcoated with a suitable gel film 27, as illustrated and described in reference to FIG. 2. Platinum black coating 26 and film 27 are grossly exaggerated in thickness in this view again for purposes of showing the discontinuous nature of both and the direct bonding of coating 26 to the metallic surface of the silver electrode. In this instance it should also be noted that the porous nature of coatings 26 and 27 permit access of the saline solution to the metallic surface of the silver electrode whereby the necessary silver chloride phase is formed in situ at the outset or before the electrophoretic analysis operation. The resulting silver chloride coating (not shown) is itself discontinuous but the operation of the electrode for its intended purposes is not impaired materially as a consequence.

Figure 4:
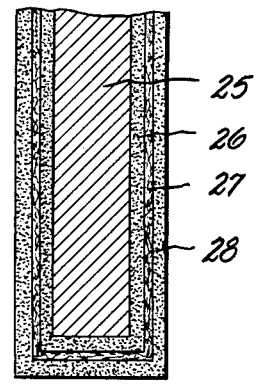
FIG. 4 is an enlarged, fragmentary cross-sectional view of a silver platinum black electrode of this invention including an overcoating of platinum black applied to the stabilizing gel coating.

The electrode of FIG. 4 is, as shown, essentially the same as that of FIG. 3 with the exception that it carries an overcoating 28 of platinum black on gel overcoat 27.

Figure 5:
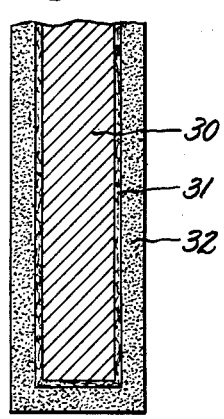
FIG. 5 is another view like those of FIGS. 2–4 of an electrode in which the silver strip is coated with a film of gel and overcoated with a layer of platinum black.
Figure 6:
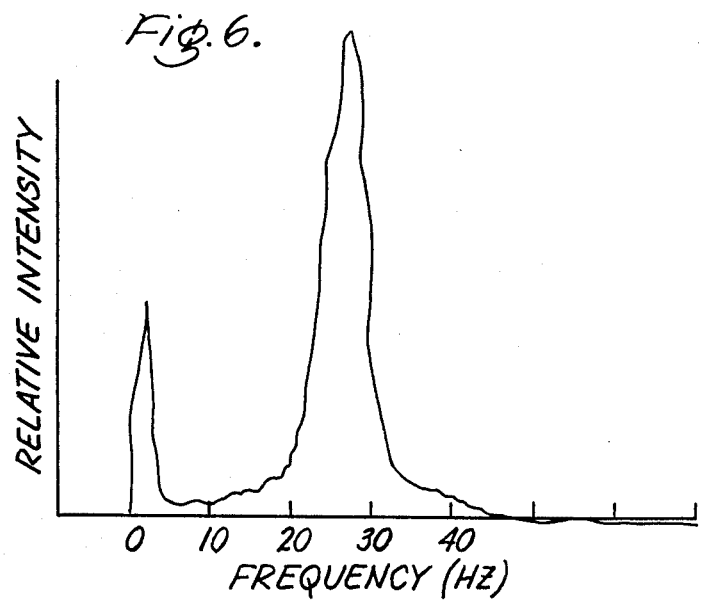
FIG. 6 is a chart on which frequency in hertz is plotted against relative intensity, the curve illustrating the ability of the equipment incorporating electrodes of this invention to produce sharply reproducible Doppler spectra at electrical fields in excess of 50 volts per centimeter, the test solution being human red blood cells in physiological saline solution of 0.15 ionic strength.

Another novel feature of this invention is illustrated in FIG. 5. Thus, silver strip 30 is provided with a gel coating 31 like coating 22 and with a platinum black overcoating 32 like overcoating 28.

If desired, metals other than silver can be used for the basic electrode element of this invention. Such metals include gold, molybdenum, and possibly palladium. Likewise, other coatings than silver chloride may be employed in the production of reversible electrophoresis electrodes of this invention. Platinum black is but one example of a material that may be used in combination with silver or other metal electrodes to provide an hybrid electrode combining the best features of platinum-platinum black electrodes and silver-silver chloride or other metal-metal compound combination electrodes.

In regard to the gel coating which is the central feature of this invention, it will be understood that while our present preference is an agarose gel, gels of other materials which are compatible in the system under the conditions of electrophoretic analysis operations can be used. An example of such other gel material, gelatin may be used to obtain the new results of this invention. In general, the gel will preferably be of a low charge polymer material and it should be applied so that it is of substantially uniform thickness overall in the range between 10 and 100 $\mu$m and has a resistivity of less than about $1.5 \times 10^{-2}$ ohm centimeter. Those skilled in the art will understand that there are a wide variety of so-called gelatinous materials that qualify under this definition and that they further have in common the characteristic of being gels in room-temperature water.

Electrodes of this invention may be prepared in any suitable manner, our preference being in respect to platinum black coatings to form them in situ by electrodeposition in a solution of chloroplatinic acid. This method works equally well whether the surface being platinized is of silver or other metal or is that of a gel layer.

The application of the gel coating may be the same irrespective of the substrates to which it is being applied, our preference being molten two percent agarose into which the electrode substrate is dipped and then either exposed to air at room temperature or is immersed in cold (suitably 15° C.) water. The gelling temperature in air is approximately 37° C. but in either air or water gelling, the gel layer formed in this manner is of desired uniformity of thickness.

WORKING EXAMPLES

The following illustrative, but not limiting, examples of our actual practice of this invention (or practice of such as it may be carried out advantageously) will serve to further illustrate the essential features of this invention for the benefit of those skilled in the art:

EXAMPLE I

A clean, freshly prepared surface of strip silver 1.5 centimeter long, two millimeters wide and 0.5 mm thick was platinized with platinum black by immersion in an aqueous five percent chloroplatinic acid solution, the silver strip being the cathode and a current of 20 milliamperes being applied. In five minutes, the silver strip was removed from the electrolyte solution, a uniform platinum coating of 25 to 50 $\mu$m having been established over its surface, and then rinsed with water and dipped in molten two percent agarose at 80° C. The agarose dip was momentary and the electrode was then exposed to air at room temperature which resulted in the agarose gelling as a film of substantially uniform thickness approximating 25 microns in 15 minutes. The resulting electrode was that illustrated in FIG. 3 and under test conditions simulating electrophoretic analysis use, the electrode did not show any surface shedding at a current density of 400 milliamperes per square centimeter over a period of one hour. A standard test solution of a phosphate buffered saline (0.15 ionic strength) was employed in simulation of such normal operating condition.

EXAMPLE II

In another experiment resembling that of Example I, silver chloride is applied to a silver strip the same as that of Example I by electrodeposition using a bath of 0.1 molar HCl aqueous solution. A gel coating about 20 μm thick was then applied to cover the resulting 25 μm-thick silver chloride layer on the strip by the agarose dipping and gelling procedure set out above. In a test as described in Example I, this electrode of FIG. 2 likewise proved to be stable against emission of particles for a one-hour period at a current density of 400 milliamperes per square centimeter.

EXAMPLE III

In another experiment like that of Example II, the electrode of FIG. 4 was prepared by immersing the gel-coated electrode of FIG. 2 in the chloroplatinic plating solution of Example I. Again, on test the resulting double-overcoated electrode proved to have the stability of the electrodes of Examples I and II.

EXAMPLE IV

A silver strip as described in Example I is provided with an agarose gel coating approximately 25 μm in thickness by the technique described above. An overcoat of platinum black is then applied to the gel-coated strip through the use of a chloroplatinic acid solution according to the Example I procedure. The resulting electrode has excellent shelf life and is ready for use or may be provided with a second overcoat of agarose gel of 10 to 100 μm thickness, as desired, before being put into use in the system of FIG. 1.

EXAMPLE V

Two electrodes prepared in accordance with Example I were used in conducting the experiment illustrated in FIG. 5, the apparatus of FIG. 1 being employed as in a manner as described above. In that particular experiment, electric fields in excess of 50 volts per centimeter were applied in obtaining a sharp, reproducible Doppler spectrum. The lack of electrode polarization permitted long duration fields of one polarity up to one second between switching events.

What we claim as new and desire to secure by Letters Patent of the United States is:

1. In a silver-silver chloride electrode for electrophoretic analysis, the combination of a porous polymer gel coating effective to prevent emission of silver chloride particles into solution during normal use in laser Doppler shift spectroscopy, said organic polymer coating having resistivity less than about $2 \times 10^{-2}$ ohm centimeter measured in physiological saline solution and being of substantially uniform thickness from 10 to 100 μm.

2. The electrode of claim 1 which is stable against surface shedding in physiological saline solution at a current density of 500 milliamperes per square centimeter.

3. The electrode of claim 1 which consists of a strip of silver about 0.5 mm in thickness bearing a coating of silver chloride.

4. The electrode of claim 1 which consists of a strip of silver bearing a porous coating of platinum black and a coating of silver chloride on surface areas exposed through the platinum black coating.

5. In a metal-metal compound electrode of a metal selected from the group consisting of silver, palladium, molybdenum, mercury and alloys and mixtures thereof useful for electrophoretic analysis, the combination of a porous polymer gel coating effective to prevent emission of electrode particles into solution during use in laser Doppler shift spectroscopy, said organic polymer coating having resistivity less than about $2 \times 10^{-2}$ ohm centimeter measured in physiological saline solution and being of substantially uniform thickness from about 10 to 100 μm.

6. The method of making an electrode useful in electrophoretic analysis by laser Doppler shift spectroscopy which comprises the steps of electrodepositing a layer of platinum black on a metal-metal compound reversible polarity electrode, applying a layer of low charge polymer gel-forming material to the resulting platinized electrode body surface, and then converting the latter said layer to gel.

7. The method of claim 6 in which the metal-metal compound electrode is a silver strip covered with silver chloride, the gel-forming material is a two percent agarose aqueous solution.

8. The method of claim 7 in which the gel-forming material is an agarose solution and conversion thereof to a gel is accomplished by cooling below the gelling temperature in water.

9. The method of making an electrode useful in electrophoretic analysis by laser Doppler shift electroscopy which comprises the steps of electrodepositing a layer of platinum black on the surface of a strip of silver, dipping the resulting platinized body into an agarose solution, and then subjecting the coated body to conditions causing the agarose adhering to the body to gel in the form of a thin film covering the body.

10. The method of claim 9 in which the electrodeposition step is carried out through the use of chloroplatinic acid as the plating solution, the agarose coating is gelled by cooling below gelling temperature, and after the gel film has thus been formed electrodepositing a second layer of platinum black of the gel film-covered electrode.

11. The method of making an electrode useful in electrophoretic analysis by laser Doppler shift spectroscopy to the surface of a strip of silver a coating of a gel of organic polymer having resistivity less than about $2 \times 10^{-2}$ ohm centimeter measured in physiological saline solution and being of substantially uniform thickness from about 10 to 100 μm, then electrodepositing a layer of platinum black on the gel coating.

* * * * *